(12) United States Patent
Hollopeter et al.

(10) Patent No.: US 11,039,899 B2
(45) Date of Patent: Jun. 22, 2021

(54) SURGICAL LIGHTING SYSTEM STERILE FIELD ENCROACHMENT INDICATOR

(71) Applicant: American Sterilizer Company, Mentor, OH (US)

(72) Inventors: Michael Hollopeter, Kirtland, OH (US); Lena T. Fogle, Fairfield, OH (US)

(73) Assignee: American Sterilizer Company, Mentor, OH (US)

( * ) Notice: Subject to any disclaimer, the term of this patent is extended or adjusted under 35 U.S.C. 154(b) by 108 days.

(21) Appl. No.: 16/145,815

(22) Filed: Sep. 28, 2018

(65) Prior Publication Data
US 2020/0100860 A1    Apr. 2, 2020

(51) Int. Cl.
 *A61B 90/35* (2016.01)
 *A61B 90/00* (2016.01)
 *A61L 2/28* (2006.01)

(52) U.S. Cl.
 CPC ............. *A61B 90/35* (2016.02); *A61B 90/08* (2016.02); *A61B 2090/081* (2016.02); *A61L 2/28* (2013.01); *A61L 2202/14* (2013.01)

(58) Field of Classification Search
 CPC . A61B 90/08; A61B 90/35; A61B 2090/0807; A61B 2090/081
 See application file for complete search history.

(56) References Cited

U.S. PATENT DOCUMENTS

| | | | |
|---|---|---|---|
| 7,009,525 B1 | 3/2006 | Shafiyan-Rad et al. | |
| 9,710,700 B2 | 7/2017 | Bilet et al. | |
| 2003/0161158 A1 | 8/2003 | Jesurun et al. | |
| 2015/0313634 A1* | 11/2015 | Gross | A61B 1/0676 606/185 |

(Continued)

FOREIGN PATENT DOCUMENTS

| | | |
|---|---|---|
| CN | 105513269 A | 4/2016 |
| CN | 205405795 U | 7/2016 |

OTHER PUBLICATIONS

International Search Report and Written Opinion issued in corresponding International Application No. PCT/US2019/048949 dated Nov. 25, 2019.

(Continued)

*Primary Examiner* — Julianna N Harvey
(74) *Attorney, Agent, or Firm* — Kusner & Jaffe

(57) ABSTRACT

A sterile field encroachment indicator apparatus for a surgical lighting system includes one or more encroachment indicators, one or more sensor units, and one or more controllers. The encroachment indicators are configured to indicate encroachment of a predetermined proximity to a surgical lighthead by a foreign entity and contact of the encroaching foreign entity with the surgical lighthead. The surgical lighthead is configured to provide illumination in order to illuminate a surgical environment. The sensor units are positioned in the surgical lighthead, and are configured to sense proximity of the foreign entity to the surgical lighthead and the contact of the encroaching foreign entity (Continued)

with the surgical lighthead. The controllers are configured to control the encroachment indicators based on the sensed proximity of the foreign entity to the surgical lighthead and the sensed contact of the foreign entity with the surgical lighthead.

21 Claims, 6 Drawing Sheets

(56) References Cited

U.S. PATENT DOCUMENTS

| | | |
|---|---|---|
| 2016/0103500 A1 | 4/2016 | Hussey et al. |
| 2016/0132122 A1 | 5/2016 | Steinle et al. |
| 2016/0184469 A1 | 6/2016 | Welch et al. |
| 2017/0112587 A1* | 4/2017 | Weiser ................. F21V 21/403 |
| 2017/0115235 A1 | 4/2017 | Ohlsson et al. |
| 2018/0209623 A1 | 7/2018 | Strölin |

OTHER PUBLICATIONS

Written Opinion issued in corresponding International Patent Application No. PCT/US2019/048949 dated Aug. 24, 2020.

International Preliminary Report on Patentability Chapter II issued in corresponding International Application No. PCT/US2019/048949 dated Nov. 17, 2020.

* cited by examiner

SURGICAL LIGHTING SYSTEM STERILE FIELD ENCROACHMENT INDICATOR

FIELD OF THE INVENTION

The present invention relates generally to an indication system for encroachment or contact of an object, and, more particularly, to a surgical lighting system sterile field encroachment indicator.

BACKGROUND OF THE INVENTION

Contamination of sterile surgical sites costs hospitals between ten and twenty thousand dollars per incident. These costs cannot be reimbursed. In particular, light handle contamination rates are high. This contamination often occurs through contact with an operative team member's cap or headgear. If the contamination is not detected, additional contact of the contaminated site by an operative team member could spread the contamination to the hands or other areas of the operative team member. The spread of contamination could inevitably lead to contamination of a surgical patient, tools used to operate on the surgical patient, or other areas of the surgical site.

Generally, the surgical staff relies on a circulating nurse to determine when a sterile field is inadvertently breached. Upon observation of the breach, the circulating nurse is charged to take appropriate remedial action. However, even though this is a primary task of the circulating nurse, it is quite possible for the breach to go partially or completely unnoticed.

The present invention provides an improved system and method for identifying and indicating that a sterile surgical lighting system has been contacted or encroached upon.

SUMMARY OF THE INVENTION

In accordance with the present invention, there is provided a sterile field encroachment indicator apparatus for a surgical lighting system. The apparatus includes one or more encroachment indicators, one or more sensor units, and one or more controllers. The encroachment indicators are configured to indicate encroachment of a predetermined proximity to a surgical lighthead by a foreign entity and contact of the encroaching foreign entity with the surgical lighthead. The surgical lighthead is configured to provide illumination in order to illuminate a surgical environment. The sensor units are positioned in the surgical lighthead, and are configured to sense proximity of the foreign entity to the surgical lighthead and the contact of the encroaching foreign entity with the surgical lighthead. The controllers are configured to control the encroachment indicators based on the sensed proximity of the foreign entity to the surgical lighthead and the sensed contact of the foreign entity with the surgical lighthead. The controllers are further configured to activate the encroachment indicators when the sensor units sense that the foreign entity has encroached the predetermined proximity to the surgical lighthead or has contacted the surgical lighthead.

In accordance with another embodiment of the present invention, there is provided a method of indicating an encroachment of a sterile field of a surgical lighthead of a surgical lighting system. A proximity of a foreign entity to the surgical lighthead is sensed, along with contact of the foreign entity with the surgical lighthead. Then, when encroachment of a predetermined proximity to the surgical lighthead by the foreign entity is sensed, encroachment of the predetermined proximity to the surgical lighthead by the foreign entity is indicated by activating one or more encroachment indicators of the surgical lighting system. In addition, when contact of the foreign entity with the surgical lighthead is sensed, contact of the foreign entity with the surgical lighthead is indicated by activating one or more of the encroachment indicators of the surgical lighting system. The indications are controlled based on the sensed proximity of the foreign entity to the surgical lighthead and the sensed contact of the foreign entity with the surgical lighthead.

In accordance with another embodiment of the present invention, there is provided a surgical lighting system. The surgical lighting system includes a surgical lighthead, one or more encroachment indicators, and one or more controllers. The surgical lighthead includes a plurality of groups of surgical light sources, a central hub, an outer ring, a neck, a handle, and one or more sensor units. The plurality of groups of surgical light sources is configured to emit light through translucent materials to illuminate a surgical environment. A first of the groups of surgical light sources is positioned within the central hub. The central hub has a translucent hub portion through which the first of the groups of surgical light sources is configured to emit light to illuminate the surgical environment. A second of the groups of surgical light sources is positioned within the outer ring that surrounds the central hub. The outer ring has a translucent ring portion through which the second of the groups of surgical light sources is configured to emit light to illuminate the surgical environment. The neck connects the central hub to the outer ring. The handle extends away from the neck. The handle is covered by a translucent handle skin. The sensor units are positioned in the one or more of the central hub, the outer ring, and the handle, and are configured to sense proximity of the foreign entity to the one or more of the central hub, the outer ring, and the handle and the contact of the encroaching foreign entity with the one or more of the central hub, the outer ring, and the handle. The encroachment indicators are configured to indicate encroachment of a predetermined proximity to the one or more of the central hub, the outer ring, and handle by the foreign entity and contact of the encroaching foreign entity with the one or more of the central hub, the outer ring, and the handle. The controllers are configured to control the encroachment indicators based on the sensed proximity of the foreign entity to the one or more of the central hub, the outer ring, and the handle and the sensed contact of the foreign entity with the one or more of the central hub, the outer ring, and the handle. The controllers are further configured to activate the encroachment indicators when the sensor units sense that the foreign entity has encroached the predetermined proximity to the one or more of the central hub, the outer ring, and the handle or has contacted the one or more of the central hub, the outer ring, and the handle.

An advantage of the present invention is to provide automatic detection of when a foreign entity, such as a surgeon's head, encroaches a predetermined proximity to the surgical lighting system.

Another advantage of the present invention is to provide automatic detection of when a foreign entity, such as a surgeon's head, contacts the surgical lighting system.

Still another advantage of the present invention is to provide a visible or an audible indication of the automatic detection to either prevent contamination or prevent the spreading of contamination from the surgical lighting system to other areas of the surgical site.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF THE INVENTION

Figure 1:
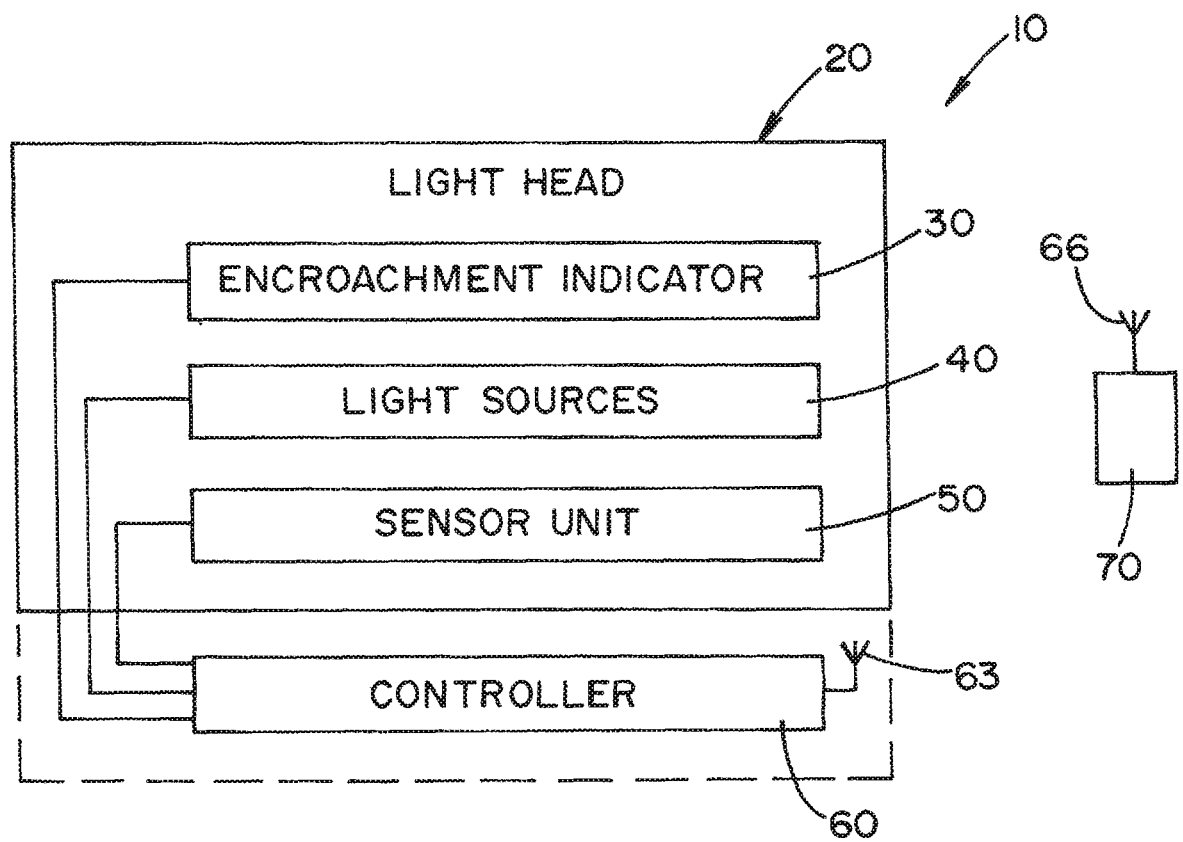
FIG. 1 is a block diagram of a surgical lighting system according to a first embodiment of the present invention
Figure 2:
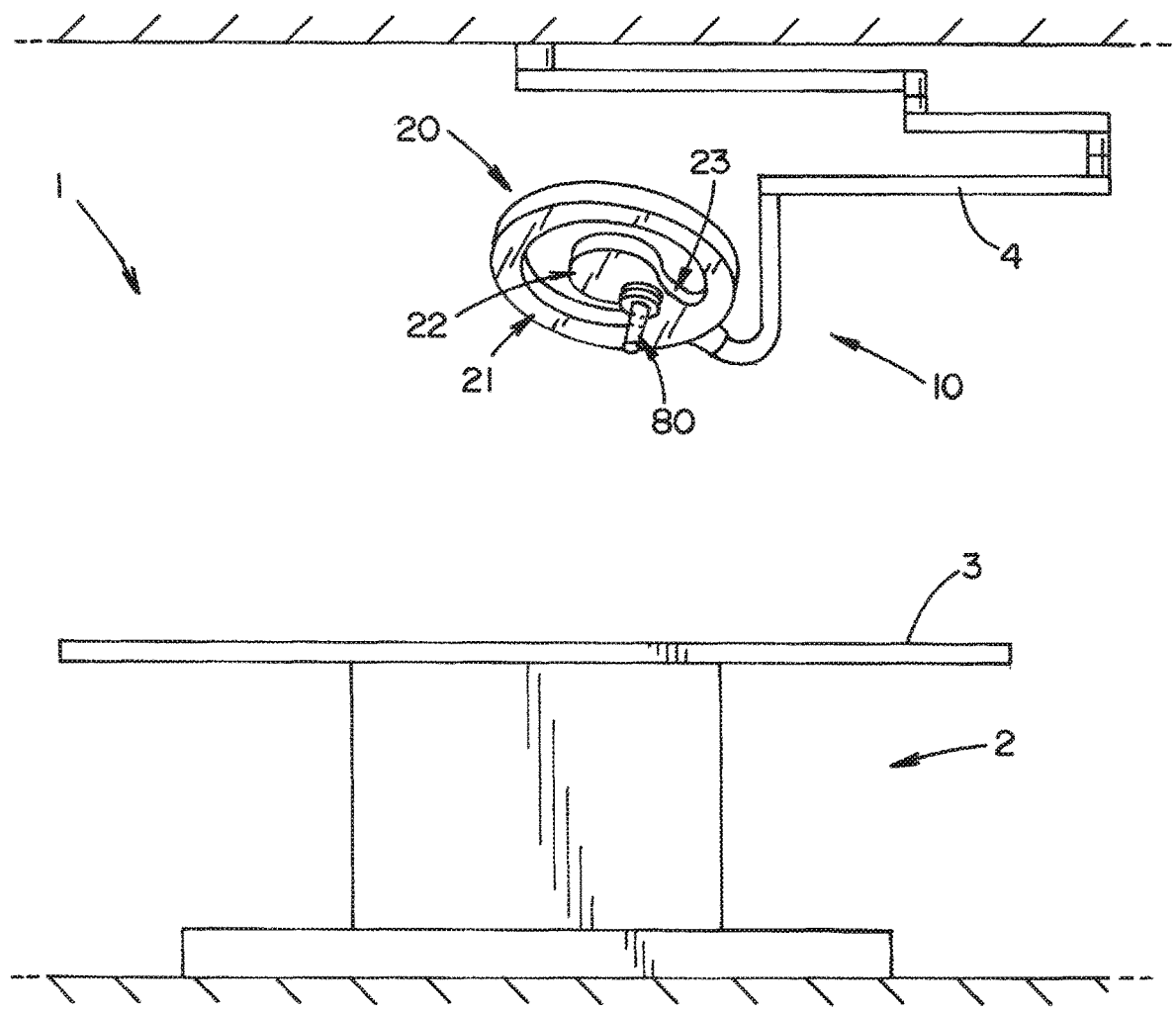
FIG. 2 is a schematic view of an example surgical lighting system positioned in a surgical environment according to a first embodiment of the present invention.
Figure 3:
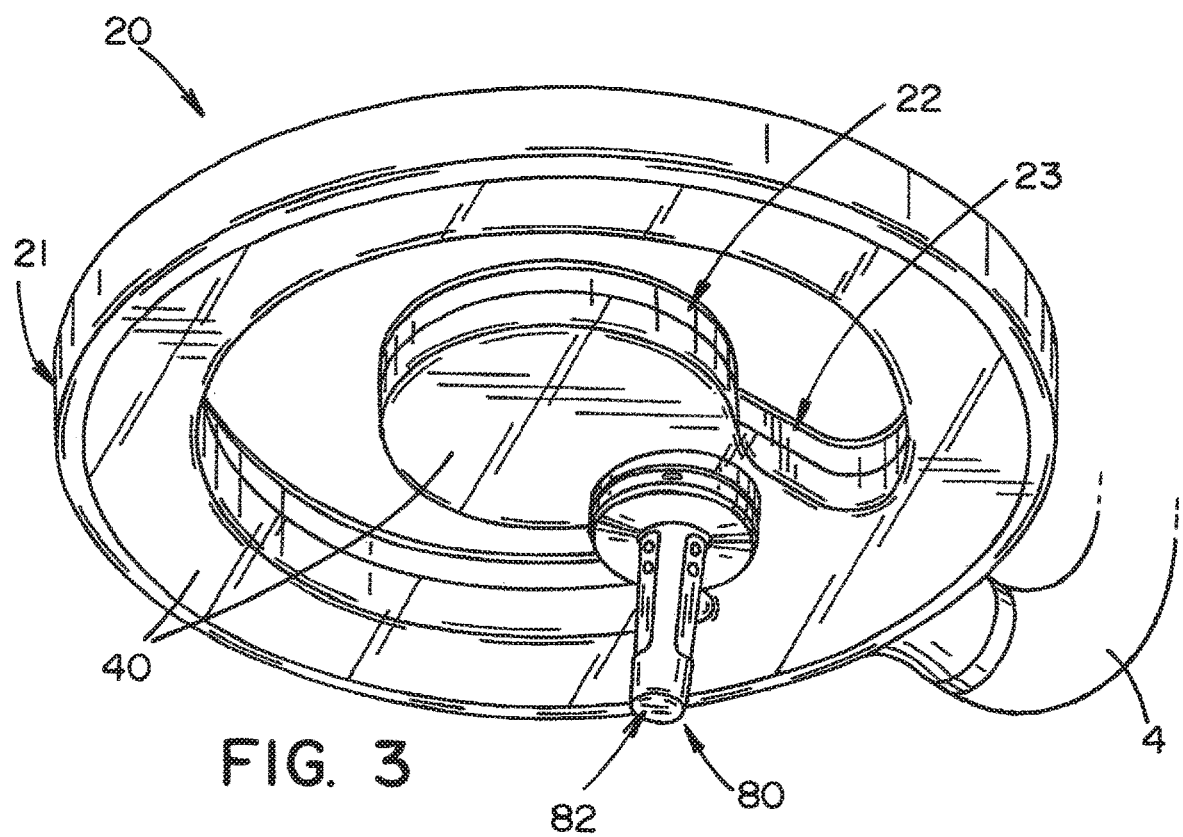
FIG. 3 is a front plan view of a surgical lighthead of a surgical lighting system according to a first embodiment of the present invention.

Referring now to the drawings wherein the showings are for the purposes of illustrating an embodiment of the invention only and not for the purposes of limiting same, FIG. 1 shows an example surgical lighting system 10 that includes a sterile field encroachment indicator according to an embodiment of the present invention. FIG. 2 provides a schematic illustration of surgical lighting system 10 positioned in surgical environment 1.

In the illustrated embodiments, surgical lighting system 10 includes surgical lighthead 20, controller 60, and user interface 70. As is shown in FIG. 2, surgical lighting system 10 also includes a support assembly for supporting surgical lighthead 20 above surgical table 2 having a work surface 3. The support assembly may take the form of a conventional suspension system 4. As known to those skilled in the art, suspension system 4 is generally comprised of a plurality of suspension arms, hubs, mounts, yokes, and the like. Suspension system 4 is configured to allow repositioning of surgical lighthead 20 relative to work surface 3 of surgical table 2.

Surgical lighthead 20 is configured to provide illumination in order to illuminate surgical environment 1. As is illustrated in FIGS. 1-8, surgical lighthead 20 is comprised of outer ring 21, central hub 22, neck 23, and handle 81. Outer ring 21 surrounds central hub 22. Neck 23 connects outer ring 21 to central hub 23. Outer ring 21 and central hub 22 both have translucent portions that face toward work surface 3 of surgical table 2. At least one encroachment indicator 30, a plurality of light sources 40, and at least one sensor unit 50 are incorporated into surgical lighthead 20.

Figure 4:
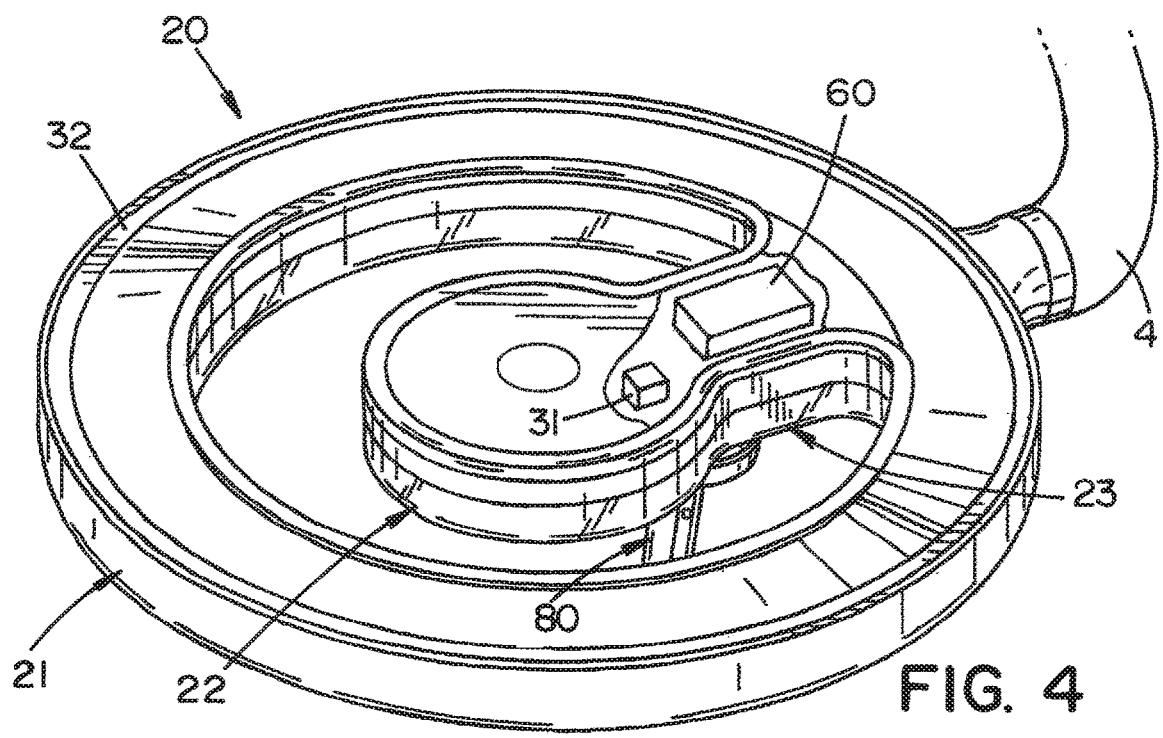
FIG. 4 is a rear plan view of a surgical lighthead of a surgical lighting system according to a first embodiment of the present invention.

Controller 60 may be a conventional microprocessor-based computer system that is in communication with various accessory devices of surgical lighthead 20 and surgical lighting system 10 (e.g., light sources 40, encroachment indicator 30, sensor unit 50, etc.). Controller 60 may be positioned in or on surgical lighthead 20. As is illustrated in FIG. 4, controller 60 may be positioned in neck 23 of surgical lighthead 20. Controller 60 and user interface 70 are illustrated in FIG. 1 as communicating with each other via wireless access points 63 and 66.

It is noted, however, that embodiments disclosed herein are not limited to the aforementioned controller arrangement. As illustrated in FIG. 1, controller 60 may be positioned remotely from surgical lighthead 20 somewhere else within surgical lighting system 10. Further, while not specifically illustrated, it is contemplated that user interface 70 may be integrated into controller 60, in which case wireless access points 63 and 66 could be used for respective communication between surgical lighthead 20 and controller 60. Moreover, there may be multiple controllers 60 spread throughout surgical lighting system 10. The controllers 60 may be programmed to share control responsibilities or perform specific control responsibilities.

User interface 70 may allow surgical staff to program controller 60. Controller 60 may be programmed in a variety of different ways. For example, controller 60 may be programmed to activate one or more encroachment indicators 30 in surgical lighthead 20 or within surgical lighting system 10 in response to receipt of certain data from one or more sensors units 50 that foreign entity 90 has encroached on a proximity of surgical lighthead 20 or contacted surgical lighthead 20. Encroachment indicators 30 and sensor units 50 will be discussed in further detail herebelow.

User interface 70 may take the form of an interface device, such as a touchscreen, a control panel, a keypad, a remote control, a wall-mount control, and the like. While illustrated in FIGS. 1 and 2 to be a wireless device, user interface 70 is not limited thereto, and may be a wired device.

Light sources 40 are best illustrated in FIGS. 3 and 6-8. Each of light sources 40 may take the form of a plurality of light emitting device (hereinafter referred to as "LED") lighting modules or pods. Light sources 40 are contained in bottom portions of outer ring 21 and central hub 22 facing toward work surface 3 of surgical table 2. The bottom portions of outer ring 21 and central hub 22 are covered with translucent material. Light is produced from each of light sources 40 that is suitable for transmission through the translucent material of outer ring 21 and central hub 22 in order to illuminate surgical environment 1 in which a surgical procedure is conducted. The illumination of surgical environment 1 by light sources 40 includes the illumination of work surface 3 of surgical table 2 on which surgical procedure is conducted.

Figure 6:
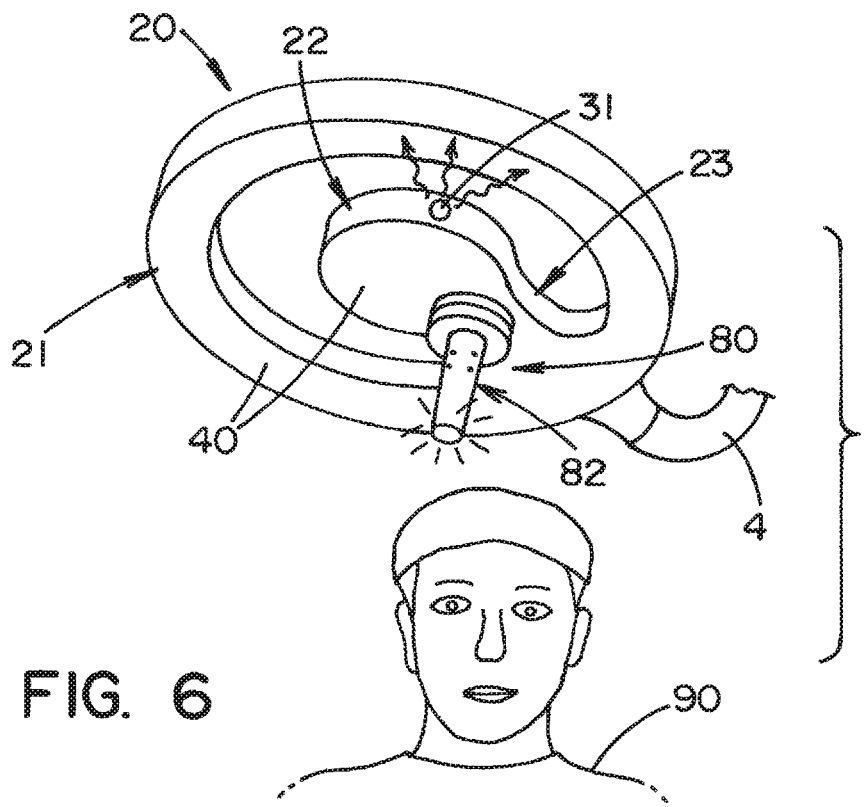
FIG. 6 is a plan view of a surgical lighthead of a surgical lighting system according to a first embodiment of the present invention, in which a foreign entity has encroached a predetermined proximity to the surgical lighting system and encroachment indicators are activated in response thereto.
Figure 7:
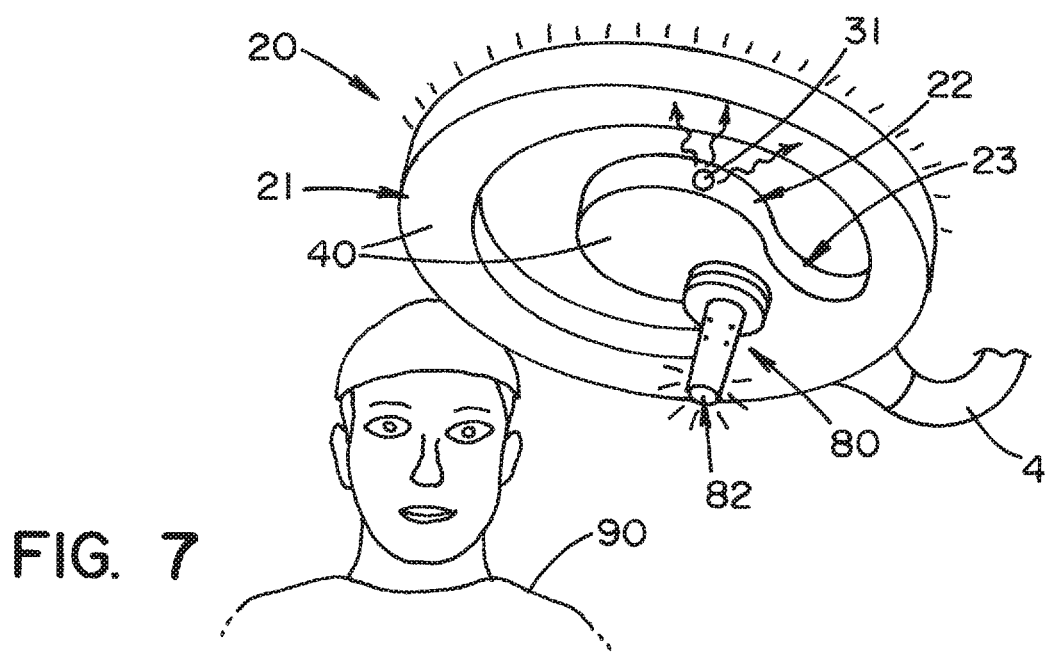
FIG. 7 is a plan view of a surgical lighthead of a surgical lighting system according to a first embodiment of the present invention, in which a foreign entity has contacted an outer area of the surgical lighting system and encroachment indicators are activated in response thereto.

At least one encroachment indicator 30 may be positioned at various areas within surgical lighthead 20 or surgical lighting system 10 and incorporated into elements of surgical lighthead 20 or surgical lighting system 10 that additionally serve other purposes. For example, encroachment indictor 30 may also be located in controller 60. In addition, encroachment indicator 30 may take many different forms. Further, encroachment indicator 30 may be controlled to indicate different types of encroachment, such as proximity encroachment, as illustrated in FIG. 6, or contact encroachment, as illustrated in FIG. 7. Moreover, encroachment indicator 30 may be deactivated automatically or manually, as illustrated in FIG. 8.

One example of encroachment indicator 30 takes the form of at least one audible alarm 31. Audible alarm 31, as is illustrated in FIGS. 3 and 6-8, may be incorporated in central hub 22. However, audible alarm 31 may be incorporated into outer ring 21, neck 23, or separately from surgical lighthead 20 in other areas of surgical lighting system 10 within surgical environment 1. Audible alarm 31 may be controlled to indicate different types of encroachment by increasing and decreasing in volume in an incremental fashion or intermittently sounding at varying audible and periodical frequencies when necessary.

In addition, as specifically illustrated in FIG. 4 and alluded to in FIG. 7, encroachment indicator 30 may take the form of accent lighting apparatus 32. Accent lighting apparatus 32 may be positioned in a circumferential channel formed in an upper surface of outer ring 21, which faces away from surgical table 2. Accent lighting apparatus 32 may include accent LEDs of a first color and accent LEDs of a second color. Light from accent LEDs of accent lighting apparatus 32 is directed in a direction that is opposite from a direction in which light from light sources 40 is directed. While not illustrated, accent lighting apparatus 32 may also be incorporated into an upper surface of central hub 22 or an upper surface of neck 23. Light from accent LEDs may be controlled to indicate different types of encroachment by increasing and decreasing in intensity in an incremental fashion or intermittently flashing at varying periodical frequencies when necessary.

Figure 5:
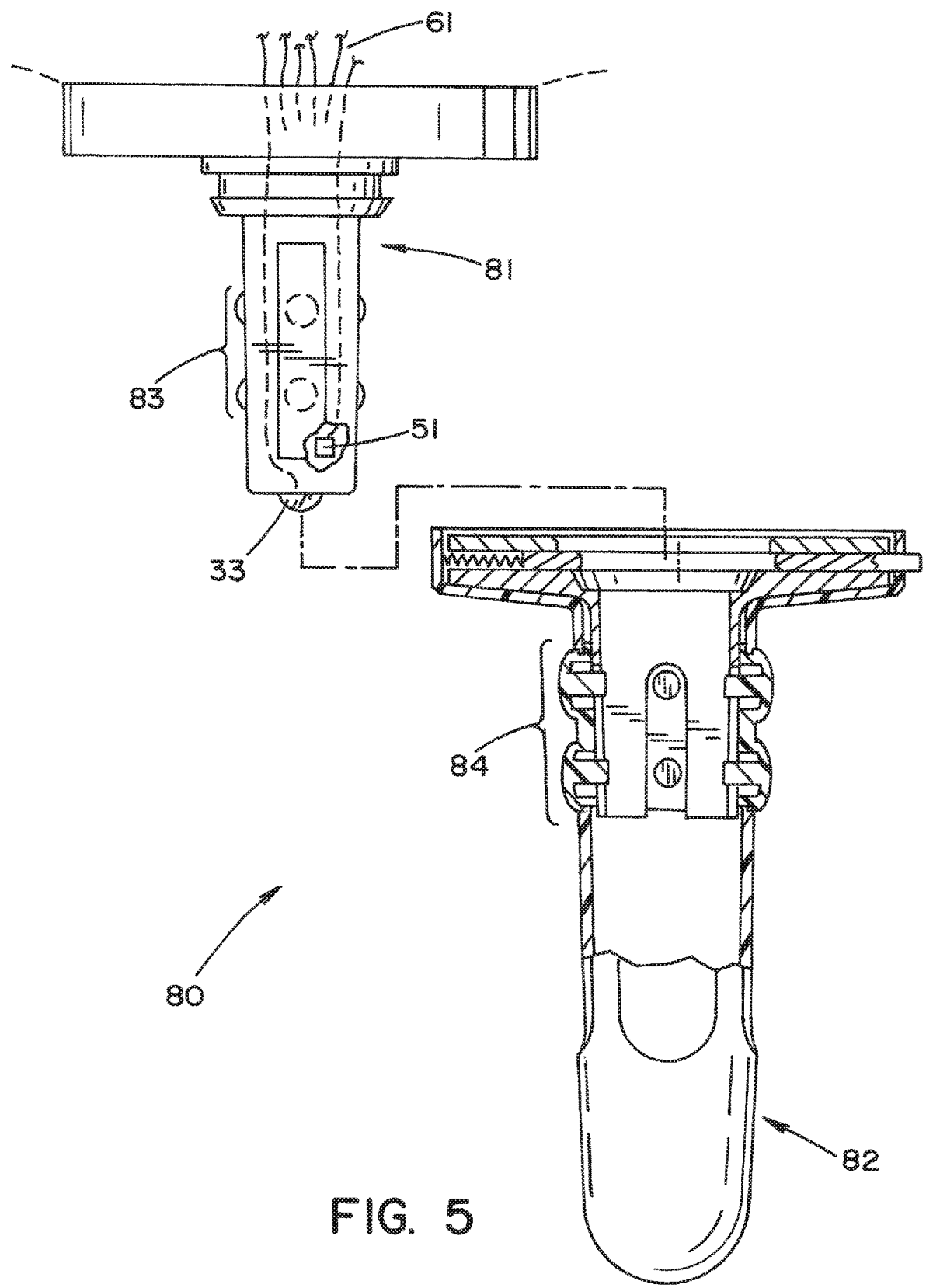
FIG. 5 is an exploded view of a handle of a surgical lighthead of a surgical lighting system according to a first embodiment of the present invention.
Figure 8:
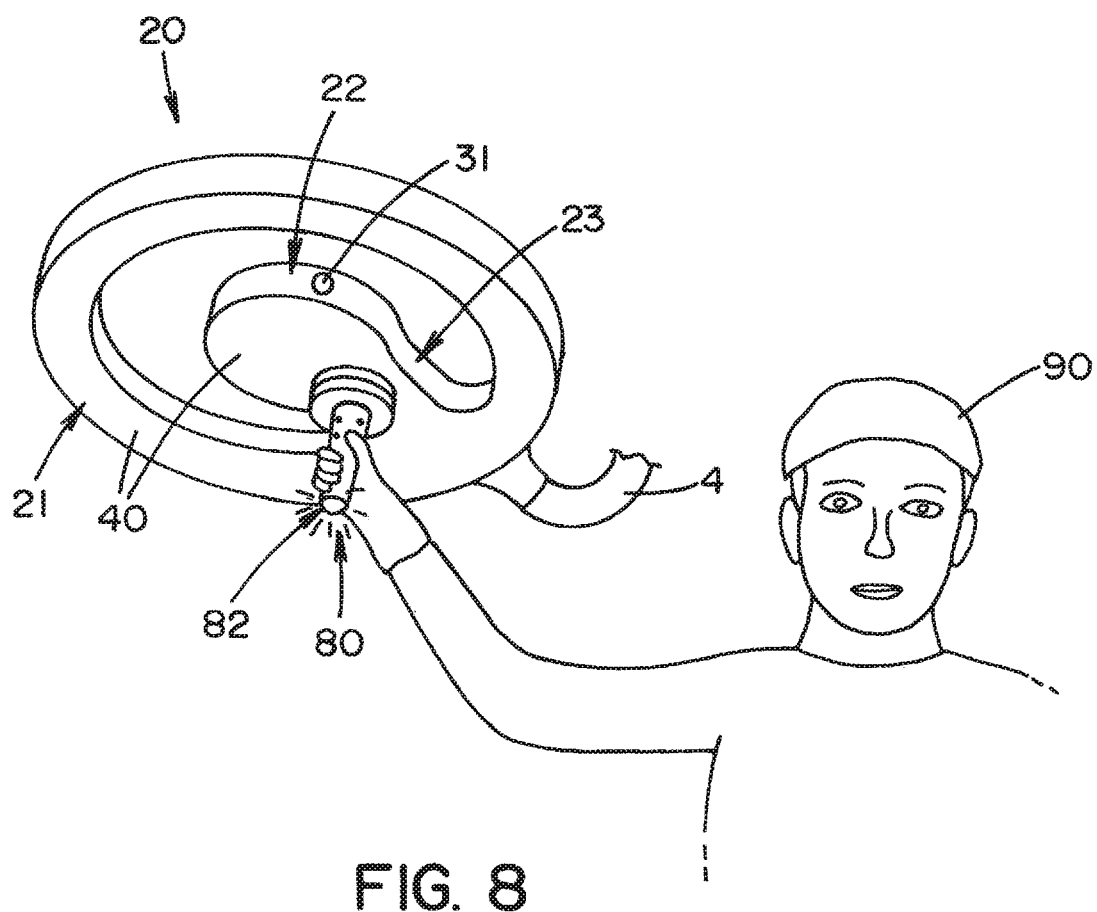
FIG. 8 is a plan view of a surgical lighthead of a surgical lighting system according to a first embodiment of the present invention, in which a foreign entity has contacted a handle of the surgical lighthead of the surgical lighting system and encroachment indicators are activated in response thereto.

Further, as specifically illustrated in FIG. 5 and alluded to in FIGS. 6-8, encroachment indicator 30 may take the form of at least one colored LED 33 that is incorporated into handle 81, which extends from neck 23 of surgical lighthead 20. Handle 81 is part of handle apparatus 80, which also includes translucent handle skin 82. Colored LED 33 is configured to emit light from handle 81 through translucent handle skin 82, thereby causing a glowing of translucent handle skin 82. Light from colored LED 33 may be controlled to indicate different types of encroachment by increasing and decreasing in intensity in an incremental fashion or intermittently flashing at varying periodical frequencies when necessary.

It is noted that encroachment indicator 30 is not limited to audible alarm 31, accent lighting apparatus 32, and colored LED 33. Moreover, encroachment indicator 30 may take the form of an intermittent periodical flashing of light sources 40. As previously mentioned, encroachment indicators 30 may be positioned remotely in various locations in surgical lighting system 10 within surgical environment 1 and activated by controller 60.

At least one sensor unit 50 is positioned in surgical lighthead 20. Sensor unit 50 may take many different forms, operate in various different ways, and utilize various different types of technology. For example, sensor unit 50 may be one or more proximity sensors positioned in surgical lighthead 20. Proximity sensors may continuously sample surgical environment 1 to detect the presence of foreign entity 90 and sense the proximity of foreign entity 90 to surgical lighthead 20. Proximity sensors may be, but are not limited to, infrared distance sensors, ultrasonic transceivers, or laser transceivers.

In another example, sensor unit 50 may be one or more contact sensors positioned in surgical lighthead 20. Contact sensors may sense contact of foreign entity 90 with surgical lighthead 20. Contact sensors may be, but are not limited to, pressure sensitive resistors or capacitive touch sensors.

In addition, a single sensor unit 50 may be equipped to provide proximity sensing and contact sensing. For example, as is illustrated in FIG. 5, combination sensor unit 51 having proximity sensing, and contact sensing may be incorporated into handle 81. Combination sensor unit 51 may provide proximity sensing and contact sensing relative to handle apparatus 80, including translucent handle skin 82. However, combination sensor unit 51 may also provide proximity sensing and contact sensing to other areas of surgical lighthead 20, including, but not limited to outer ring 21, central hub 22, and neck 23.

While FIG. 5 illustrates a single combination sensor unit 51, embodiments disclosed herein are not limited thereto. For example, while not illustrated, separate proximity and contact sensors may be placed on handle 81 to perform sensing independent of each other. Moreover, a plurality of sensor units that are either combination sensor units or separate proximity and contact sensors may be positioned in multiple areas throughout surgical lighthead 20, including, but not limited to, outer ring 21 and central hub 21, such that proximity and contact may be optimally sensed in any desired area of surgical lighthead 20.

FIG. 5 illustrates an example of a means by which colored LED 33 and combination sensor unit 51 positioned within handle 81 may be communicatively connected to controller 60 illustrated in FIG. 4 as being positioned in central hub 22. A plurality of wiring 61 may be used to establish communicative connections between controller 60 in central hub 22 and components positioned within handle 81, such as, for example, combination sensor unit 51, colored LED 33, and handle control interface 83.

Handle control interface 83 may be utilized to provide local and immediate control to components encompassed within surgical lighthead 20. For example, handle control interface 83 may be utilized to adjust light color or intensity of light sources 40, light color or intensity of accent LEDs in accent lighting apparatus 32, light color or intensity of colored LED 33, sensitivity of combination sensor unit 51 or other sensor units disposed within surgical lighthead 20, and volume of audible alarm 31. Further, handle control interface 83 may be used to acknowledge and cease any indication of encroachment provided by encroachment indicators 30.

Apart from having a translucent property that allows colored LED 33 to indicate encroachment therethrough, translucent handle skin 82 serves to protect the components of handle 81 from contamination. For example, when surgical lighthead 20 is in need of repositioning, a surgeon will take hold of sterile translucent handle skin 82 of handle apparatus 80 in order to enact such repositioning. Further, translucent handle skin 82 includes handle control interface pad 84, which enables a user to control surgical lighthead 20 via handle control interface 83 without needing direct access to handle control interface 83, thereby avoiding damage or contamination of the components of handle 81.

Translucent handle skin 82 can be removed from neck 23 and handle 81. The removability of translucent handle skin 82 serves several purposes. Upon contamination, translucent handle skin 82 may be disposed and replaced with another translucent handle skin 82.

Foreign entity 90 may be anything that could result in contamination of surgical lighthead 20. A non-limiting example of foreign entity 90 is illustrated in FIGS. 6-8, in which foreign entity 90 is represented by a person that is presumably involved in a surgical procedure under surgical lighthead 20. The particular person representing foreign entity 90 may be a surgeon, a nurse, or any other professional that may be present in surgical environment 1 during execution of a surgical procedure. As is illustrated in FIG. 8, foreign entity 90 could be a hand of the person encroaching on handle 80 of surgical lighthead 20, which will be further discussed below. As is illustrated in FIGS. 6 and 7, foreign entity 90 could be the surgical cap of the person. However, embodiments described herein are not limited thereto. For example, foreign entity 90 may be any article that may conceivably contaminate a portion of surgical lighthead 20.

While embodiments are not limited thereto, the operation of surgical lighting system 10 and particular scenarios that might occur during such operation will now be discussed with respect to the features illustrated in FIGS. 3-8. As such, light sources 40 are incorporated into outer ring 21 and central hub 22. Accent lighting assembly 32 is incorporated into outer ring 21. While audible alarm 31 and controller 60 may be incorporated into other areas of surgical lighting system 10 if preferred, in the illustrated embodiments, audible alarm 31 and controller 60 are incorporated into surgical lighthead 20 of surgical lighting system 10. Handle assembly 80, including handle 81, combination sensor unit 51, colored LED 33, handle control interface 83, translucent skin handle 82, and handle control interface pad 84, is mounted on and extends from neck 23. Foreign entity 90 is a surgeon or nurse using surgical lighthead 20 for visibility in surgical environment 1 while performing an operation on a subject positioned on work surface 3 of surgical table 2.

Initially, controller 60 may be used by a surgeon or nurse to define a predetermined proximity of surgical lighthead 20 at which encroachment indicators 30 will be activated when foreign entity 90 enters therewithin. A surgeon or nurse may input the predetermined proximity parameters into controller 60 or control sensitivity of combination sensor unit 51 by operating handle control interface pad 84 through handle control interface 83, user interface 70, or other means not illustrated that may be provided in surgical lighting system 10.

Handle control interface pad 84 and handle control interface 83 or, alternatively, user interface 70 may be further used by a surgeon or nurse to program controller 60 to activate specific encroachment indicators 30 with specific reactions in response to specific occurrences. For example, controller 60 may be programmed to illuminate accent lighting assembly 32 or increase the illumination emitted from accent lighting assembly 32 in response to encroachment of the predetermined proximity of surgical lighthead 20. Controller 60 may also be programmed to quickly cycle accent lighting assembly 32 on and off when contact of surgical lighthead 20 with foreign entity 90 is detected. Alternatively, controller 60 may be programmed to operate first As another example, one group of encroachment indicators 30 may be dedicated to proximity alerts, while another group of encroachment indicators 30 may be dedicated to contact alerts. Handle control interface pad 84 and handle control interface 83 or user interface 70 may allow further programming of controller 60 to adjust light color or intensity of colored LED 33, volume, frequency, and intermittent sounding of audible alarm 31, and intermittent flashing of light sources 40 in response to specific occurrences.

Moreover, controller 60 may be programmed to activate one group of encroachment indicators 30 for a proximity breach and another group of encroachment indicators 30 when contact with surgical lighthead 20 is detected. For example, proximity breaches may be indicated by light emitting devices of a first color in any location in which light emitting devices are used as encroachment indicators 30. Contact with surgical lighthead 20, on the other hand, may be indicated by light emitting devices of a second color in any location in which light emitting devices are used as encroachment indicators 30.

In addition, controller 60 may be programmed to activate particular encroachment indicators 30 to specifically indicate contact with translucent handle skin 82 has occurred. Such an indication would allow a surgeon or nurse to simply remove translucent handle skin 82 and replace it within another like translucent handle skin 82 that is sterilized.

Handle control interface pad 84 and handle control interface 83 or user interface 70 may also be used by the surgeon or nurse to activate the sterile field encroachment indicator when so desired. When activated, sensor unit 51 and controller 60 monitor the predetermined proximity of surgical lighthead 20 for foreign entity 90. Activated sensor unit 51 and controller 60 are also able to detect contact of foreign entity 90 with surgical lighthead 20.

When controller 60 determines that data has been received from sensor unit 51 indicating foreign entity 90 to be within the predetermined proximity to surgical lighthead 20, controller 60 activates encroachment indicators 30 in accordance with its programming for proximity alerts. When data received from sensor unit 51 leads controller 60 to determine that the encroaching foreign entity 90 has moved outside the predetermined proximity to surgical lighthead 20 without having contacted surgical lighthead 20, controller 60 deactivates encroachment indicators 30.

When controller 60 determines that data has been received from sensor unit 51 indicating that the encroaching foreign entity 90 has contacted surgical lighthead 20, controller 60 activates encroachment indicators 30 in accordance with its programming for contact alerts. In such a situation, controller 60 allows encroachment indicators 30 to remain activated for a predetermined period or until the activated encroachment indicators 30 are manually deactivated by operation of controller 60 by a surgeon or nurse through handle control interface pad 84 and handle control interface 83 or user interface 70.

The foregoing descriptions are example embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A sterile field encroachment indicator apparatus for a surgical lighting system, the apparatus comprising:
  one or more encroachment indicators configured to indicate encroachment of a predetermined proximity to a surgical lighthead by a foreign entity and contact of the encroaching foreign entity with the surgical lighthead, the surgical lighthead being configured to provide illumination in order to illuminate a surgical environment, one or more of the encroachment indicators being positioned in a handle of the surgical lighthead that is covered by a translucent handle skin;

one or more sensor units positioned in the surgical lighthead, the sensor units being configured to sense proximity of the foreign entity to the surgical lighthead and the contact of the encroaching foreign entity with the surgical lighthead; and one or more controllers configured to control the encroachment indicators based on the sensed proximity of the foreign entity to the surgical lighthead and the sensed contact of the foreign entity with the surgical lighthead, the controllers being further configured to activate the encroachment indicators when the sensor units sense that the foreign entity has at least one of encroached the predetermined proximity to the surgical lighthead or contacted the surgical lighthead.

2. The apparatus according to claim 1, wherein the controllers are further configured to deactivate the encroachment indicators when the sensor units sense that the encroaching foreign entity moves outside of the predetermined proximity to the surgical lighthead without having contacted the surgical lighthead.

3. The apparatus according to claim 1, wherein, when the sensor units sense the contact of the encroaching foreign entity with the surgical lighthead, the encroachment indicators are activated by the controller and remain activated for a predetermined period of time or until the activated encroachment indicators are manually deactivated.

4. The apparatus according to claim 1, wherein the encroachment indicators comprise:

one or more proximity alerts configured to indicate the encroachment of the predetermined proximity to the surgical lighthead by the foreign entity; and one or more contact alerts configured to indicate the contact of the encroaching foreign entity with the surgical lighthead.

5. The apparatus according to claim 4, wherein the controllers are further configured to deactivate the proximity alerts when the sensor units sense that the encroaching foreign entity has moved outside of the predetermined proximity to the surgical lighthead without having contacted the surgical lighthead or has contacted the surgical lighthead, and wherein, when the sensor units sense the contact of the encroaching foreign entity with the surgical lighthead, the contact alerts are activated by the controller and remain activated for a predetermined period or until the activated contact alerts are manually deactivated.

6. The apparatus according to claim 5, wherein the sensor units comprise:

one or more proximity sensors configured to sense the proximity of the foreign entity to the surgical lighthead; and one or more contact sensors configured to sense the contact of the encroaching foreign entity with the surgical lighthead, and wherein the controllers are further configured to control:
the proximity alerts based on the proximity sensed by the proximity sensors; and
the contact alerts based on the contact sensed by the contact sensor.

7. The apparatus according to claim 1, wherein the sensor units comprise:

one or more proximity sensors positioned in the surgical lighthead, the proximity sensors being configured to sense the proximity of the foreign entity to the surgical lighthead; and one or more contact sensors positioned in the surgical lighthead, the contact sensors being configured to sense the contact of the encroaching foreign entity with the surgical lighthead, and wherein the controllers are further configured to control the encroachment indicators based on the proximity sensed by the proximity sensors and the contact sensed by the contact sensor.

8. The apparatus of claim 7, wherein the proximity sensors comprise at least one of the group consisting of one or more infrared distance sensors, one or more ultrasonic transceivers, and one or more laser transceivers.

9. The apparatus of claim 7, wherein the contact sensors comprise at least one of the group consisting of one or more pressure sensitive resistors and one or more capacitive touch sensors.

10. The apparatus according to claim 1, wherein one or more of the encroachment indicators are surgical light sources positioned in the surgical lighthead, the surgical light sources being configured to illuminate a surgical environment in which a surgical procedure is conducted, and wherein the controllers are further configured to flash the surgical light sources when the sensor units sense that the foreign entity contacts the surgical lighthead.

11. The apparatus according to claim 1, wherein one or more of the encroachment indicators are audible alarms, and wherein the controllers are further configured to activate the audible alarms when the sensor units sense that the foreign entity has encroached the predetermined proximity to the surgical lighthead or has contacted the surgical lighthead.

12. The apparatus of claim 1, wherein the encroachment indicators positioned in the handle of the surgical lighthead comprise one or more light emitting devices of a first color, and wherein the controllers are further configured to activate the first color light emitting devices to cause a glowing of the translucent handle skin when the sensor units sense that the foreign entity has encroached the predetermined proximity to the surgical lighthead or has contacted the surgical lighthead.

13. The apparatus of claim 1, wherein the encroachment indicators positioned in the handle of the surgical lighthead are configured to indicate encroachment of a predetermined proximity to the translucent handle skin by the foreign entity and contact of the encroaching foreign entity with the translucent handle skin, and wherein the sensor units are configured to sense:
proximity of the foreign entity to the translucent handle skin; and
the contact of the encroaching foreign entity with the translucent handle skin.

14. The apparatus of claim 13, wherein at least one of the sensor units is positioned in the handle.

15. The apparatus of claim 14, wherein the controllers are configured to control the encroachment indicators based on the sensed proximity of the foreign entity to the translucent handle skin and the sensed contact of the foreign entity with the translucent handle skin, the controllers being configured to activate the encroachment indicators when the sensor units sense that the foreign entity has encroached the predetermined proximity to the translucent handle skin or has contacted the translucent handle skin.

16. The apparatus of claim 1, wherein one or more of the encroachment indicators are positioned in the surgical lighthead as an accent lighting apparatus that is configured to provide accent lighting for an area in which a surgical procedure is conducted, the accent lighting apparatus comprising:
   accent light emitting devices of a first color; and
   accent light emitting devices of a second color,
   wherein, when the sensor units do not sense that the foreign entity has encroached the predetermined proximity to the surgical lighthead or has contacted the surgical lighthead, the controllers are configured to illuminate the first color accent light emitting devices, and
   wherein, when the sensor units sense that the foreign entity has encroached the predetermined proximity to the surgical lighthead, the controllers are configured to illuminate the second color accent light emitting devices, and
   wherein, when the sensor units sense that the foreign entity has contacted the surgical lighthead, the controllers are configured to intermittently illuminate the second color accent light emitting devices.

17. The apparatus of claim 16, wherein the accent lighting apparatus is positioned in a circumferential channel of an upper surface of an outer ring of the surgical lighthead, and
   wherein light from the accent lighting apparatus is directed in a direction that is opposite from a direction in which light from the light sources is directed.

18. The apparatus according to claim 1, wherein at least one of the controllers is positioned in the surgical lighthead.

19. A sterile field encroachment indicator apparatus for a surgical lighting system, the apparatus comprising:
   one or more encroachment indicators configured to indicate encroachment of a predetermined proximity to a surgical lighthead by a foreign entity and contact of the encroaching foreign entity with the surgical lighthead, the surgical lighthead being configured to provide illumination in order to illuminate a surgical environment, the encroachment indicators comprising:
      one or more proximity alerts configured to indicate the encroachment of the predetermined proximity to the surgical lighthead by the foreign entity; and
      one or more contact alerts configured to indicate the contact of the encroaching foreign entity with the surgical lighthead;
   one or more sensor units positioned in the surgical lighthead, the sensor units being configured to sense proximity of the foreign entity to the surgical lighthead and the contact of the encroaching foreign entity with the surgical lighthead; and
   one or more controllers configured to control the encroachment indicators based on the sensed proximity of the foreign entity to the surgical lighthead and the sensed contact of the foreign entity with the surgical lighthead, the controllers being further configured to activate the encroachment indicators when the sensor units sense that the foreign entity has at least one of encroached the predetermined proximity to the surgical lighthead or contacted the surgical lighthead,
   wherein one or more of the proximity alerts comprises a plurality of light emitting devices of a first color, and
   wherein, when the proximity alert is activated, an intensity of each of the light emitting devices of the first color is dynamically controlled by the controllers based on a relative proximity of the encroaching foreign entity to the surgical lighthead between the predetermined proximity of the foreign entity to the surgical lighthead and the contact of the foreign entity with the surgical lighthead.

20. The apparatus according to claim 19, wherein one of more of the contact alerts comprises a plurality of light emitting devices of a second color, and
   wherein, when the contact alert is activated by the controllers, the proximity alert is deactivated by the controllers.

21. A method of indicating an encroachment of a sterile field for a surgical lighting system, the method comprising:
   indicating, with one or more encroachment indicators, encroachment of a predetermined proximity to a surgical lighthead by a foreign entity and contact of the encroaching foreign entity with the surgical lighthead, the surgical lighthead providing illumination in order to illuminate a surgical environment, one or more of the encroachment indicators being positioned in a handle of the surgical lighthead that is covered by a translucent handle skin;
   sensing, with one or more sensor units positioned in the surgical lighthead, proximity of the foreign entity to the surgical lighthead and the contact of the encroaching foreign entity with the surgical lighthead; and
   controlling, with one or more controllers, the encroachment indicators based on the sensed proximity of the foreign entity to the surgical lighthead and the sensed contact of the foreign entity with the surgical lighthead, the controlling comprising activating the encroachment indicators when the sensing senses that the foreign entity has at least one of:
   encroached the predetermines proximity to the surgical lighthead; and
   contacted the surgical lighthead.

* * * * *